United States Patent
Bayani

(10) Patent No.: US 9,420,821 B2
(45) Date of Patent: *Aug. 23, 2016

(54) DRINKING WATER FORMULATION AND METHOD AND ARTICLE RELATING TO SAME

(71) Applicant: ESSENTIALIFE HOMEOPATHICS, Atlanta, GA (US)

(72) Inventor: Ramin Stephan Bayani, Atlanta, GA (US)

(73) Assignee: Essentialife Homeopathics, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/078,221

(22) Filed: Mar. 23, 2016

(65) Prior Publication Data

US 2016/0198755 A1 Jul. 14, 2016

Related U.S. Application Data

(63) Continuation of application No. 13/561,053, filed on Jul. 29, 2012, now Pat. No. 9,307,783, which is a continuation-in-part of application No. 12/392,382, filed on Feb. 25, 2009, now abandoned.

(60) Provisional application No. 61/031,095, filed on Feb. 25, 2008.

(51) Int. Cl.
*A23L 2/52* (2006.01)
*B65D 51/28* (2006.01)
(Continued)

(52) U.S. Cl.
CPC . *A23L 2/395* (2013.01); *A23L 2/40* (2013.01); *A61K 9/14* (2013.01); *A61K 31/04* (2013.01);
(Continued)

(58) Field of Classification Search
USPC .......... 426/590, 648, 74, 72, 66, 115, 85, 112
See application file for complete search history.

(56) References Cited

U.S. PATENT DOCUMENTS 4,515,805 A   5/1985   Newman et al.
5,238,686 A   8/1993   Eichel et al.
(Continued)

FOREIGN PATENT DOCUMENTS

EP   0687466 A1    12/1995
WO   9904759 A1     2/1999
WO   2007069845 A1  6/2007

OTHER PUBLICATIONS aquasana. Live Healthy, http://www.aquasana.com/product_detail.php?product_id=43, May 2014, pp. 1-2, Publisher: Aquasana, Inc.
(Continued)

*Primary Examiner* — Erik Kashnikow
*Assistant Examiner* — Lela S Williams
(74) *Attorney, Agent, or Firm* — Hultquist PLLC; Mary B. Grant

(57) ABSTRACT

Homeopathic water compositions are described, as well as beverage articles for making drinking water formulations with such compositions. One such beverage article includes a water bottle, and a dispensing cap adapted to be secured to the water bottle. The dispensing cap contains dried homeopathic composition-coated sucrose or sucrose/starch particles that are dispensable into water in the water bottle by user actuation of the dispensing cap, to constitute the homeopathic water formulation for consumption.

20 Claims, 3 Drawing Sheets

(51) Int. Cl.
          A23L 2/395      (2006.01)
          A61K 31/137     (2006.01)
          A61K 36/886     (2006.01)
          A61K 33/36      (2006.01)
          A61K 36/48      (2006.01)
          A61K 36/71      (2006.01)
          A61K 36/42      (2006.01)
          A61K 35/583     (2015.01)
          A61K 36/68      (2006.01)
          A61K 33/26      (2006.01)
          A61K 31/04      (2006.01)
          A61K 36/484     (2006.01)
          A61K 36/23      (2006.01)
          A61K 33/18      (2006.01)
          A61K 36/88      (2006.01)
          A61K 36/11      (2006.01)
          A61K 33/14      (2006.01)
          A61K 36/56      (2006.01)
          A61K 36/22      (2006.01)
          A61K 36/75      (2006.01)
          A61K 36/15      (2006.01)
          A61K 35/55      (2015.01)
          A61K 36/28      (2006.01)
          A61K 9/14       (2006.01)
          B05D 1/02       (2006.01)
          A23L 2/40       (2006.01)
          B65B 7/16       (2006.01)

(52) U.S. Cl.
     CPC ............ *A61K 31/137* (2013.01); *A61K 33/14* (2013.01); *A61K 33/18* (2013.01); *A61K 33/26* (2013.01); *A61K 33/36* (2013.01); *A61K 35/55* (2013.01); *A61K 35/583* (2013.01); *A61K 36/11* (2013.01); *A61K 36/15* (2013.01); *A61K 36/22* (2013.01); *A61K 36/23* (2013.01); *A61K 36/28* (2013.01); *A61K 36/42* (2013.01); *A61K 36/48* (2013.01); *A61K 36/484* (2013.01); *A61K 36/56* (2013.01); *A61K 36/68* (2013.01); *A61K 36/71* (2013.01); *A61K 36/75* (2013.01); *A61K 36/88* (2013.01); *A61K 36/886* (2013.01); *B05D 1/02* (2013.01); *B65B 7/16* (2013.01); *A23V 2002/00* (2013.01)

(56) References Cited

U.S. PATENT DOCUMENTS

| | | | |
|---|---|---|---|
| 5,922,378 | A | 7/1999 | Kagan et al. |
| 6,471,971 | B1 | 10/2002 | Wollenweber et al. |
| 7,378,015 | B2 | 5/2008 | Rinker et al. |
| 2002/0162458 | A1 | 11/2002 | Farr et al. |
| 2007/0178123 | A1 | 8/2007 | Levenson et al. |
| 2007/0193894 | A1 | 8/2007 | Macken et al. |
| 2008/0190827 | A1 | 8/2008 | Rinker et al. |
| 2009/0214711 | A1 | 8/2009 | Bayani |
| 2013/0008807 | A1 | 1/2013 | Bayani |

OTHER PUBLICATIONS

An Interview with Dr. Luc: Getting started with Homeopathy and FAQ's, http://www.drluc.com/homeopathy-basics.htm, May 2007, pp. 1-6, Publisher: DrLuc.com.

Homeopathic remedies in water, homopathyeandmore.com/forum/viewtopic.php?t=1203, Apr. 17, 2007, pp. 1-3.

Schmukler, A., "Homeopathy: An A to Z Home Handbook", Jul. 8, 2006, pp. 42-43, Publisher: Llewellyn Publications, Published in: Woodbury, Minnesota.

Royal London Hospital for Integrated Medicine: Homeopathy and homeopathic medicines, http://www.uclh.nhs.uk/PandV/PIL/Patient%20information%20leaflets/Homeopathy%20and%20homeopathic%20medicines.pdf, 2007, pp. 1-16, Publisher: University College London Hospitals NHS Foundation Trust 2013.

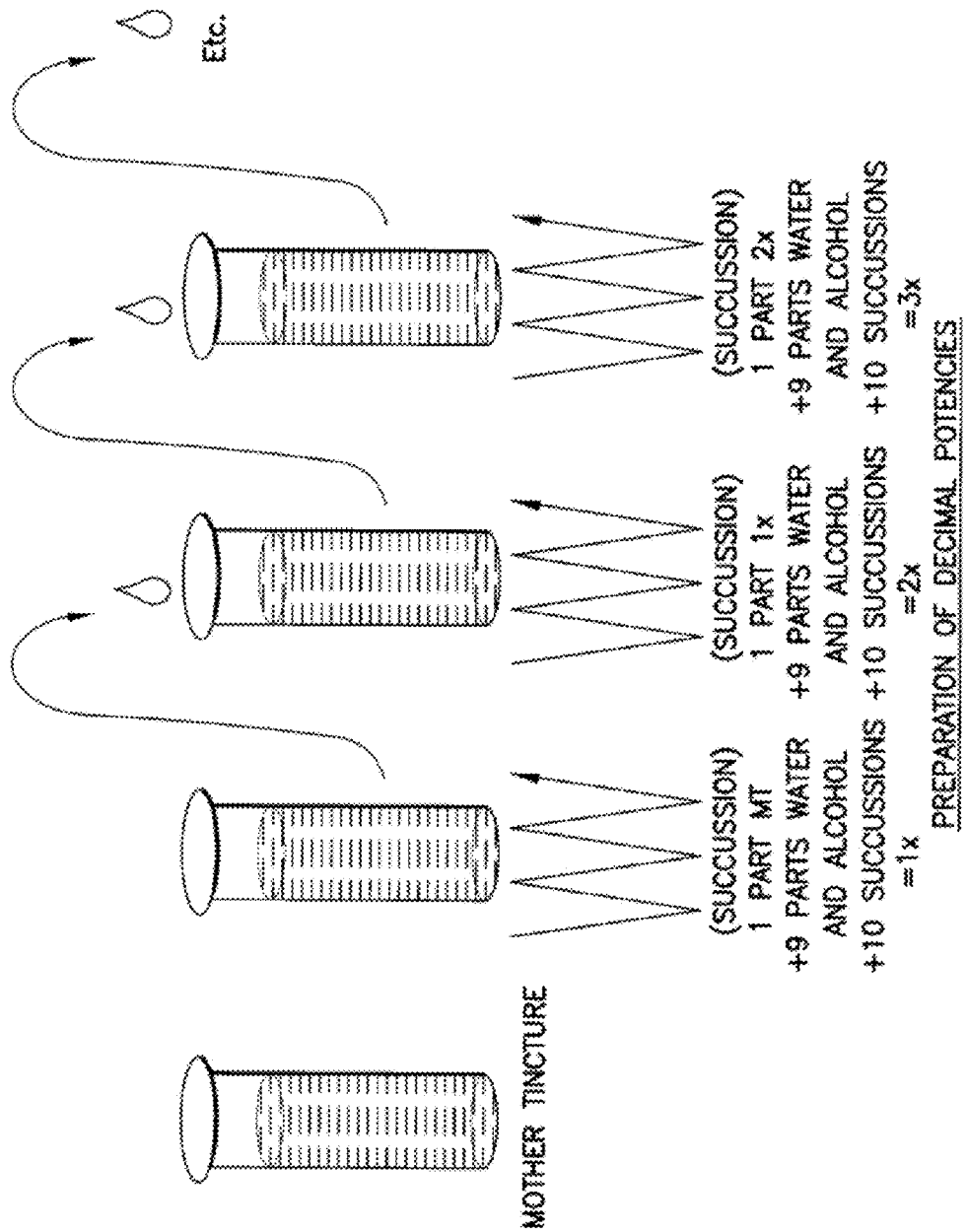

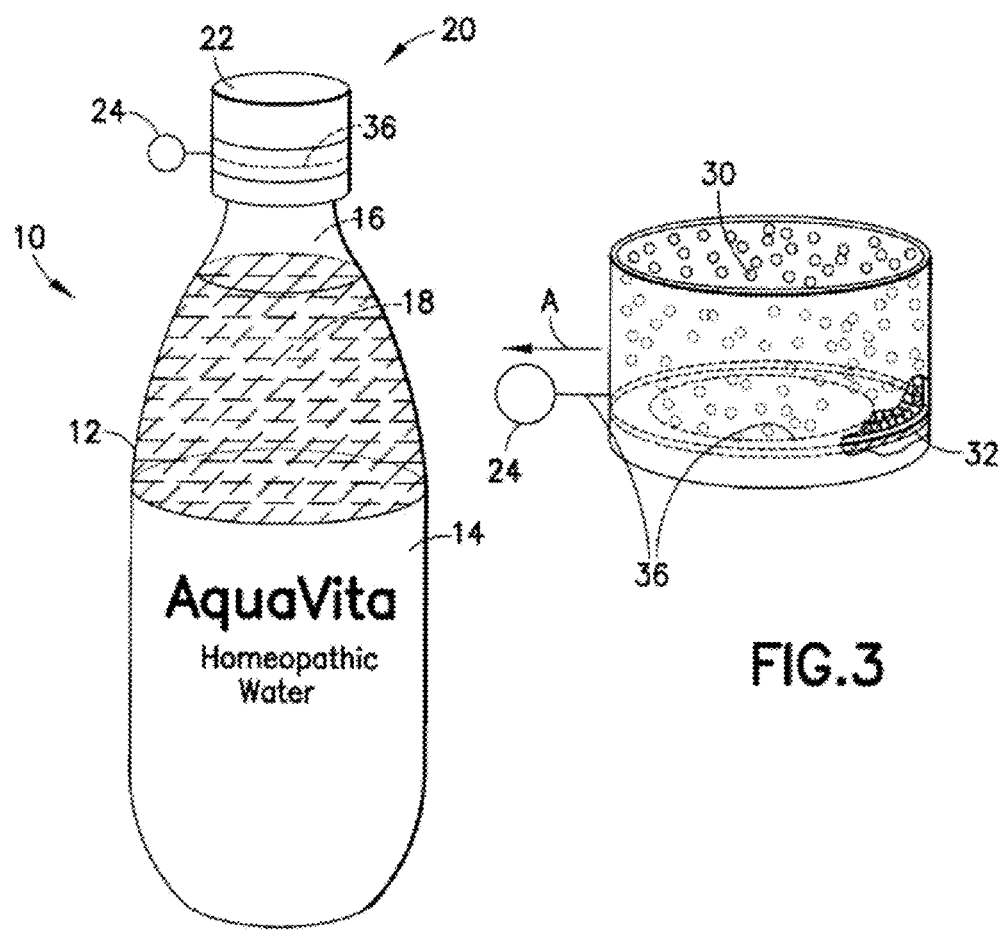

DRINKING WATER FORMULATION AND METHOD AND ARTICLE RELATING TO SAME

CROSS REFERENCE TO RELATED APPLICATION

This is a continuation of U.S. patent application Ser. No. 13/561,053 filed on Jul. 29, 2012, which in turn is a continuation-in-part under 35 USC 120 of U.S. patent application Ser. No. 12/392,382 filed Feb. 25, 2009, which in turn claims the benefit under 35 USC 119 of U.S. Provisional Patent Application No. 61/031,095 filed Feb. 25, 2008. The disclosure of U.S. patent application Ser. No. 13/561,053; U.S. patent application Ser. No. 12/392,382; and U.S. Provisional Patent Application No. 61/031,095 are hereby incorporated herein by reference in their respective entireties, for all purposes.

FIELD

The present disclosure relates to drinking water formulations containing homeopathic ingredients, to beverage articles including such drinking water formulations, and to methods for making and using such drinking water formulations and beverage articles.

DESCRIPTION OF THE RELATED ART

Consumers have been increasingly attracted to specialty waters and water formulations for drinking purposes. Natural spring waters and carbonated waters are ubiquitous, and in recent years a variety of enhanced water beverages have been commercialized. Such water products include formulations containing a variety of flavors and aromatic ingredients.

There is an increasing public awareness of the health benefits of maintaining active hydration through water consumption, and an increased sophistication related to drinking water products.

SUMMARY

The present disclosure relates to homeopathic ingredient-containing drinking water formulations, beverage articles including such formulations, and methods for making and using such formulations.

In one aspect, the disclosure relates to a beverage article, comprising:

a water bottle; and at least one dispensing cap adapted to be secured to the water bottle, and containing dried homeopathic composition-coated sucrose or sucrose/starch particles that are dispensable into water in the water bottle by user actuation of the dispensing cap, when the dispensing cap is secured to the water bottle containing water.

In such beverage article, the dispensing cap may be user-actuatable for dispensing the particles therefrom by manual pressure exerted on a top portion of the dispensing cap. The dried homeopathic composition-coated sucrose or sucrose/starch particles may consist of dried homeopathic composition and sucrose particles having a diameter in a range of from 500 to 2000 μm, more preferably in a range of from 1000 to 1600 μm. Alternatively, the dried homeopathic composition-coated sucrose or sucrose/starch particles consist of dried homeopathic composition and sucrose/starch particles having a diameter in a range of from 500 to 1000 μm, more preferably in a range of from 710 to 850 μm.

The foregoing beverage articles of the disclosure may comprise a multiplicity of the dispensing caps, wherein the water bottle is reusable with respective ones of the multiplicity of dispensing caps. When the dried homeopathic composition-coated sucrose or sucrose/starch particles consist of dried homeopathic composition and sucrose particles, each of the multiplicity of dispensing caps may contain a same homeopathic composition in the dried homeopathic composition-coated sucrose particles, or the multiplicity of dispensing caps may contain a different homeopathic composition in the dried homeopathic composition-coated sucrose particles. Likewise, when the dried homeopathic composition-coated sucrose or sucrose/starch particles consist of dried homeopathic composition and sucrose/starch particles, each of the multiplicity of dispensing caps may contain a same homeopathic composition in the dried homeopathic composition-coated sucrose/starch particles, or each of the multiplicity of dispensing caps may contain a different homeopathic composition in the dried homeopathic composition-coated sucrose/starch particles.

In the beverage articles of the disclosure, the dried homeopathic composition-coated sucrose or sucrose/starch particles may comprise a homeopathic composition selected from the group consisting of:

(a) a homeopathic composition of *Adrenalinum* 15×, *Aloe* 15×, *Arsenicum alb.* 15×, *Baptisia* 15×, *Berber. aqui.* 15×, *Berber. vulg.* 15×, *Bryonia* 15×, *Chelidonium majus* 15×, *Crotalus horridus* 15×, *Digitalis* 15×, *Ferrum metallicum* 15×, *Glonoinum* 15×, *Glycyrrhiza glabra* 15×, *Hydrocotyle* 15×, *Iodium* 15×, *Iris versicolor* 15×, *Lachesis* 15×, *Lycopodium* 15×, *Nat. mur.* 15×, *Nux vom.* 15×, *Rhus toxicodendron* 15×, *Ruta* 15×, *Thuja occ.* 15×, *Thyroidinum* 15×, *Echinacea* 3×, *Lappa* 3×, *Solidago* 3×, *Taraxacum* 3×;

(b) a homeopathic composition of *Arsenicum alb.* 15×, *Benzoicum acidum* 15×, *Berber. vulg* 15×, *Bryonia* 15×, *Caladium seguinum* 15×, *Cantharis* 15×, *Ceanothus* 15×, *Chelidonium majus* 15×, *Chionanthus virginica* 15×, *Cinchona* 15×, *Daphne indica* 15×, *Ignatia* 15×, *Iris versicolor* 15×, *Lycopodium* 15×, *Nicotinum* 15×, *Nux vom.* 15×, *Rhus toxicodendron* 15×, *Scutellaria laterifolia* 15×, *Tabacum* 15×, *Echinacea* 3×, *Taraxacum* 3×, *Valeriana* 3×;

(c) a homeopathic composition of *Aconitum nap.* 15×, *Antimon. tart.* 15×, *Arg. nit.* 15×, *Arnica* 15×, *Bryona* 15×, *Chamomilla* 15×, *Chelidonium majus* 15×, *Cimicifuga* 15×, *Eupatorium perf.* 15×, *Hypericum* 15×, *Nux vom.* 15×, *Rhus toxicodendron* 15×, *Ruta* 15×, *Sarcolacticum ac.* 15×, *Stramonium* 15×, *Strychnium* 15×, *Chamomilla* 3×, *Phytolacca* 3×, *Ruta* 3×, *Symphytum* 3×;

(d) a homeopathic composition of *Aconitum nap.* 15×, *Arg. nit.* 15×, *Aur. met.* 15×, *Baptisia* 15×, *Bryonia* 15×, *Chelidonium majus* 15×, *Cimicifuga* 15×, *Conium* 15×, *Gelsemium* 15×, *Ignatia* 15×, *Kali carb.* 15×, *Lachesis* 15×, *Lilum* 15×, *Lycopodium* 15×, *Nat. carb.* 15×, *Nat. mur.* 15×, *Phosphoricum ac.* 15×, *Phosphorus* 15×, *Picricum ac.* 15×, *Plumb. met.* 15×, *Sepia* 15×, *Staphysag.* 15×, *Stramonium* 15×, *Thuja occ.* 15×, *Zinc. met.* 15×, *Chamomilla* 3×, *Hypericum* 3×, *Valeriana* 3×;

(e) a homeopathic composition of *Anacardium orientale* 15×, *Antimon. crud.* 15×, *Arg. nit.* 15×, *Berber. vulg.* 15×, *Bryonia* 15×, *Chelidonium majus* 15×, *Digitalis* 15×, *Graphites* 15×, *Humulus* 15×, *Iris versicolor* 15×, *Kali carb.* 15×, *Lycopodium* 15×, *Nat. carb.* 15×, *Nat. sulphuricum* 15×, *Nux vom.* 15×, *Pulsatilla* 15×, *Rhus toxicodendron* 15×, *Scutellaria laterifolia* 15×, *Sepia* 15×, *Stramonium* 15×, *Chamomilla* 3×, *Passiflora* 3×, *Valeriana* 3×; and (f) a homeopathic composition of *Uricum acidum* 15×, *Benzoicum acidum* 10×, *Berber. vulg.* 10×, *Bryonia* 10×,

*Cantharis* 10×, *Carduus benedictus* 10×, *Ceanothus* 10×, *Chelidonium majus* 10×, *Chionanthus virginica* 10×, *Cinchona* 10×, *Dioscorea* 10×, *Dolichos* 10×, *Iris versicolor* 10×, *Juniperus com.* 10×, *Nux vom.* 10×, *Ptelea* 10×, *Taraxacum* 10×, *Carduus mar.* 3×, *Cynara scolymus* 3×, *Solidago* 3×, *Taraxacum* 3×.

In such beverage article, the dried homeopathic composition-coated sucrose or sucrose/starch particles can consist of one of:
(i) dried homeopathic composition and sucrose particles having a diameter in a range of from 1000 to 1600 μm; and
(ii) dried homeopathic composition and sucrose/starch particles having a diameter in a range of from 710 to 850 μm.

The beverage article may be constituted so that the dispensing cap contains from 0.5 to 2.5 g of the dried homeopathic composition-coated sucrose or sucrose/starch particles. The water bottle of such beverage article may be adapted to hold a volume of water that is in a range of from 200 mL to 2 liters, and more specifically in a range of from 400 to 600 mL, with the dispensing cap containing from 0.75 to 1.25 g of the dried homeopathic composition-coated sucrose or sucrose/starch particles.

The water bottle in such beverage article may contain water, or may alternatively may be packaged in an empty state with the dispensing cap.

A further aspect of the disclosure relates to a beverage article, comprising:
a water bottle; and
at least one dispensing cap adapted to be secured to the water bottle, and containing dried homeopathic composition-coated sucrose or sucrose/starch particles that are dispensable into water in the water bottle by user actuation of the dispensing cap, when the dispensing cap is secured to the water bottle containing water,
wherein the dried homeopathic composition-coated sucrose or sucrose/starch particles consist of one of:
(i) dried homeopathic composition and sucrose particles having a diameter in a range of from 1000 to 1600 μm; and
(ii) dried homeopathic composition and sucrose/starch particles having a diameter in a range of from 710 to 850 μm;
wherein the dispensing cap is user-actuatable for dispensing the particles therefrom by manual pressure exerted on a top portion of the dispensing cap;
wherein the dispensing cap contains from 0.75 to 1.25 g of the dried homeopathic composition-coated sucrose or sucrose/starch particles;
wherein the water bottle is adapted to hold a volume of water that is in a range of from 200 mL to 2 liters; and
wherein the dried homeopathic composition-coated sucrose or sucrose/starch particles comprise a homeopathic composition selected from the group consisting of:
(a) a homeopathic composition of *Adrenalinum* 15×, *Aloe* 15×, *Arsenicum alb.* 15×, *Baptisia* 15×, *Berber. aqui.* 15×, *Berber. vulg.* 15×, *Bryonia* 15×, *Chelidonium majus* 15×, *Crotalus horridus* 15×, *Digitalis* 15×, *Ferrum metallicum* 15×, *Glonoinum* 15×, *Glycyrrhiza glabra* 15×, *Hydrocotyle* 15×, *Iodium* 15×, *Iris versicolor* 15×, *Lachesis* 15×, *Lycopodium* 15×, *Nat. mur.* 15×, *Nux vom.* 15×, *Rhus toxicodendron* 15×, *Ruta* 15×, *Thuja occ.* 15×, *Thyroidinum* 15×, *Echinacea* 3×, *Lappa* 3×, *Solidago* 3×, *Taraxacum* 3×;
(b) a homeopathic composition of *Arsenicum alb.* 15×, *Benzoicum acidum* 15×, *Berber. vulg* 15×, *Bryonia* 15×, *Caladium seguinum* 15×, *Cantharis* 15×, *Ceanothus* 15×, *Chelidonium majus* 15×, *Chionanthus virginica* 15×, *Cinchona* 15×, *Daphne indica* 15×, *Ignatia* 15×, *Iris versicolor* 15×, *Lycopodium* 15×, *Nicotinum* 15×, *Nux vom.* 15×, *Rhus toxicodendron* 15×, *Scutellaria laterifolia* 15×, *Tabacum* 15×, *Echinacea* 3×, *Taraxacum* 3×, *Valeriana* 3×;
(c) a homeopathic composition of *Aconitum nap.* 15×, *Antimon. tart.* 15×, *Arg. nit.* 15×, *Arnica* 15×, *Bryona* 15×, *Chamomilla* 15×, *Chelidonium majus* 15×, *Cimicifuga* 15×, *Eupatorium perf.* 15×, *Hypericum* 15×, *Nux vom.* 15×, *Rhus toxicodendron* 15×, *Ruta* 15×, *Sarcolacticum ac.* 15×, *Stramonium* 15×, *Strychnium* 15×, *Chamomilla* 3×, *Phytolacca* 3×, *Ruta* 3×, *Symphytum* 3×;
(d) *a homeopathic composition of Aconitum nap.* 15×, *Arg. nit.* 15×, *Aur. met.* 15×, *Baptisia* 15×, *Bryonia* 15×, *Chelidonium majus* 15×, *Cimicifuga* 15×, *Conium* 15×, *Gelsemium* 15×, *Ignatia* 15×, *Kali carb.* 15×, *Lachesis* 15×, *Lilum* 15×, *Lycopodium* 15×, *Nat. carb.* 15×, *Nat. mur.* 15×, *Phosphoricum ac.* 15×, *Phosphorus* 15×, *Picricum ac.* 15×, *Plumb. met.* 15×, *Sepia* 15×, *Staphysag.* 15×, *Stramonium* 15×, *Thuja occ.* 15×, *Zinc. met.* 15×, *Chamomilla* 3×, *Hypericum* 3×, *Valeriana* 3×;
(e) a homeopathic composition of *Anacardium orientale* 15×, *Antimon. crud.* 15×, *Arg. nit.* 15×, *Berber. vulg.* 15×, *Bryonia* 15×, *Chelidonium majus* 15×, *Digitalis* 15×, *Graphites* 15×, *Humulus* 15×, *Iris versicolor* 15×, *Kali carb.* 15×, *Lycopodium* 15×, *Nat. carb.* 15×, *Nat. sulphuricum* 15×, *Nux vom.* 15×, *Pulsatilla* 15×, *Rhus toxicodendron* 15×, *Scutellaria laterifolia* 15×, *Sepia* 15×, *Stramonium* 15×, *Chamomilla* 3×, *Passiflora* 3×, *Valeriana* 3×; and
(f) a homeopathic composition of *Uricum acidum* 15×, *Benzoicum acidum* 10×, *Berber. vulg.* 10×, *Bryonia* 10×, *Cantharis* 10×, *Carduus benedictus* 10×, *Ceanothus* 10×, *Chelidonium majus* 10×, *Chionanthus virginica* 10×, *Cinchona* 10×, *Dioscorea* 10×, *Dolichos* 10×, *Iris versicolor* 10×, *Juniperus com.* 10×, *Nux vom.* 10×, *Ptelea* 10×, *Taraxacum* 10×, *Carduus mar.* 3×, *Cynara scolymus* 3×, *Solidago* 3×, *Taraxacum* 3×.

In another aspect, the disclosure relates to an aqueously soluble or dispersible composition comprising dried homeopathic composition-coated sucrose or sucrose/starch particles, including a homeopathic composition selected from the group consisting of:
(a) a homeopathic composition of *Adrenalinum* 15×, *Aloe* 15×, *Arsenicum alb.* 15×, *Baptisia* 15×, *Berber. aqui.* 15×, *Berber. vulg.* 15×, *Bryonia* 15×, *Chelidonium majus* 15×, *Crotalus horridus* 15×, *Digitalis* 15×, *Ferrum metallicum* 15×, *Glonoinum* 15×, *Glycyrrhiza glabra* 15×, *Hydrocotyle* 15×, *Iodium* 15×, *Iris versicolor* 15×, *Lachesis* 15×, *Lycopodium* 15×, *Nat. mur.* 15×, *Nux vom.* 15×, *Rhus toxicodendron* 15×, *Ruta* 15×, *Thuja occ.* 15×, *Thyroidinum* 15×, *Echinacea* 3×, *Lappa* 3×, *Solidago* 3×, *Taraxacum* 3×;
(b) a homeopathic composition of *Arsenicum alb.* 15×, *Benzoicum acidum* 15×, *Berber. vulg* 15×, *Bryonia* 15×, *Caladium seguinum* 15×, *Cantharis* 15×, *Ceanothus* 15×, *Chelidonium majus* 15×, *Chionanthus virginica* 15×, *Cinchona* 15×, *Daphne indica* 15×, *Ignatia* 15×, *Iris versicolor* 15×, *Lycopodium* 15×, *Nicotinum* 15×, *Nux vom.* 15×, *Rhus toxicodendron* 15×, *Scutellaria laterifolia* 15×, *Tabacum* 15×, *Echinacea* 3×, *Taraxacum* 3×, *Valeriana* 3×;
(c) a homeopathic composition of *Aconitum nap.* 15×, *Antimon. tart.* 15×, *Arg. nit.* 15×, *Arnica* 15×, *Bryona* 15×, *Chamomilla* 15×, *Chelidonium majus* 15×, *Cimicifuga* 15×, *Eupatorium perf.* 15×, *Hypericum* 15×, *Nux vom.* 15×, *Rhus toxicodendron* 15×, *Ruta* 15×, *Sarcolacticum ac.* 15×, *Stramonium* 15×, *Strychnium* 15×, *Chamomilla* 3×, *Phytolacca* 3×, *Ruta* 3×, *Symphytum* 3×;
(d) a homeopathic composition of *Aconitum nap.* 15×, *Arg. nit.* 15×, *Aur. met.* 15×, *Baptisia* 15×, *Bryonia* 15×, *Chelidonium majus* 15×, *Cimicifuga* 15×, *Conium* 15×, *Gelsemium* 15×, *Ignatia* 15×, *Kali carb.* 15×, *Lachesis* 15×, *Lilum* 15×,

*Lycopodium* 15×, *Nat. carb.* 15×, *Nat. mur.* 15×, *Phosphoricum ac.* 15×, *Phosphorus* 15×, *Picricum ac.* 15×, *Plumb. met.* 15×, *Sepia* 15×, *Staphysag.* 15×, *Stramonium* 15×, *Thuja occ.* 15×, *Zinc. met.* 15×, *Chamomilla* 3×, *Hypericum* 3×, *Valeriana* 3×;

(e) a homeopathic composition of *Anacardium orientale* 15×, *Antimon. crud.* 15×, *Arg. nit.* 15×, *Berber. vulg.* 15×, *Bryonia* 15×, *Chelidonium majus* 15×, *Digitalis* 15×, *Graphites* 15×, *Humulus* 15×, *Iris versicolor* 15×, *Kali carb.* 15×, *Lycopodium* 15×, *Nat. carb.* 15×, *Nat. sulphuricum* 15×, *Nux vom.* 15×, *Pulsatilla* 15×, *Rhus toxicodendron* 15×, *Scutellaria laterifolia* 15×, *Sepia* 15×, *Stramonium* 15×, *Chamomilla* 3×, *Passiflora* 3×, *Valeriana* 3×; and (f) a homeopathic composition of *Uricum acidum* 15×, *Benzoicum acidum* 10×, *Berber. vulg.* 10×, *Bryonia* 10×, *Cantharis* 10×, *Carduus benedictus* 10×, *Ceanothus* 10×, *Chelidonium majus* 10×, *Chionanthus virginica* 10×, *Cinchona* 10×, *Dioscorea* 10×, *Dolichos* 10×, *Iris versicolor* 10×, *Juniperus com.* 10×, *Nux vom.* 10×, *Ptelea* 10×, *Taraxacum* 10×, *Carduus mar.* 3×, *Cynara scolymus* 3×, *Solidago* 3×, *Taraxacum* 3×, wherein the dried homeopathic composition-coated sucrose or sucrose/starch particles consist of one of:

(i) dried homeopathic composition and sucrose particles having a diameter in a range of from 1000 to 1600 µm; and (ii) dried homeopathic composition and sucrose/starch particles having a diameter in a range of from 710 to 850 µm.

A further aspect of the disclosure relates to a method of making a homeopathic drinking water formulation, comprising mixing an aqueous medium with an aqueously soluble or dispersible composition of the present disclosure.

Other aspects, features and embodiments of the disclosure will be more fully apparent from the ensuing description and appended claims.

BRIEF DESCRIPTION OF THE DRAWINGS

FIG. 1 is a schematic representation of a process of preparing a homeopathic composition of a mother tincture starting material, involving successive dilution and sucession steps, to achieve homeopathic potentization of a homeopathic component.

FIG. 2 is a perspective view of a beverage article according to one embodiment of the disclosure.

FIG. 3 is an enlarged, partially broken-away view, in perspective, of the cap of the FIG. 2 beverage article.

DETAILED DESCRIPTION, AND PREFERRED EMBODIMENTS THEREOF

Figure 4:
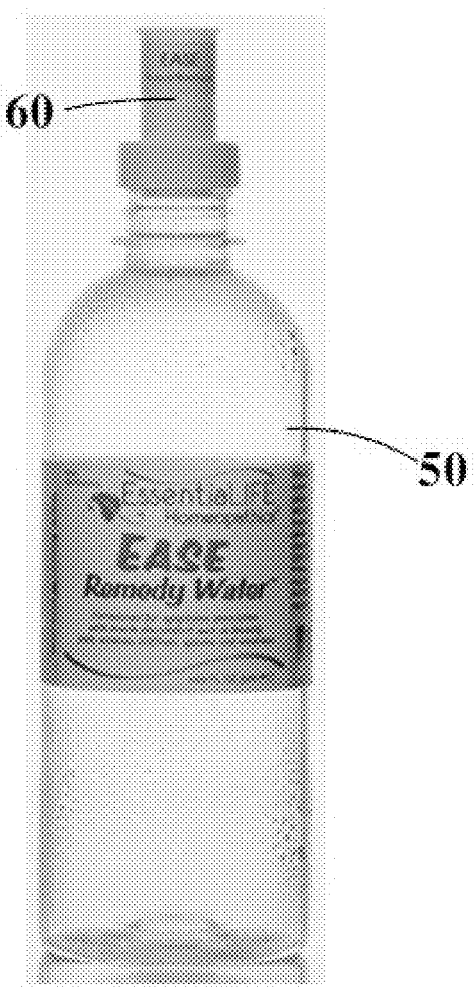
FIG. 4 is a front elevation view of a beverage article according to another embodiment of the disclosure.

The present disclosure relates to drinking water formulations containing homeopathic ingredients, to beverage articles including such drinking water formulations, and to methods for making and using such drinking water formulations and beverage articles. The homeopathic water formulations and beverage articles of the present disclosure are useful in healthful consumption of drinking water and for homeopathic applications for which homeopathic ingredients are effective.

In contrast to many homeopathic remedies made by traditional methods, homeopathic ingredients in the formulations of the present disclosure can be made for subsequent consumption in an alcohol-free form, to produce drinking water formulations that are usefully constituted at the time of use for consumption, as well as drinking water formulations that can be bottled in beverage containers to provide packaged water formulations useful for general consumer use.

Homeopathic ingredients have been developed in various disciplines, to provide remedies for maladies and physiological conditions such as fatigue, feminine ailments, undesired hair conditions, excessive or deficient appetite, immunological deficiency, joint and muscle pain, undesired skin conditions, stress, anxiety, and accumulation of toxins in the body.

Homeopathic ingredients have varied natural sources, including plants, minerals, and animal sources.

Set out below is an illustrative listing of physiological conditions and applications, and illustrative homeopathic ingredients that may be useful for same, according to various specific embodiments of the disclosure.

Appetite Control: *anacardium orientale, calcarea carbonica, chelidonium majus, fucus vesiculosus, graphites naturalis, guarana (paullina sorbilis* HPUS), *iodium purum, lycopodium clavatum, natrum sulphuricum, pulsatilla nigricans, sulphur iodatum, thyroidin um;* 10×.

Fatigue Relief: *alfalfa, ambra grisea, aurum metallicum, avena sativa, caladium seguinum, calcarea carbonica, cocculus indicus, gelsemium sempervirens, kali phosphoricum, phosphoricum acidurm, selenium, silicea terra;* 10×.

Feminine: *agnus castus, aletris farinose, berberis vulgaris, caulophyllum thalictroides, ferrum metallicum, graphites naturalis, helonias dioica, ignatia arnara, lilium tigrinurn, lycopodium clavaturm, natrum muriaticum, onosrmodium virginianum, pulsatilla nigricans, sepia succus;* 10×.

Hair Care: *adrenalinum, antimonium crudurm, arsenicum album, borax veneta, fluoricum acidurm, graphites naturalis, kali carbonicum, natrum rnuriaticurn, nitricum acidum, phosphoricum acidum, phosphorus, pix liquida, selenium, sepia succus, silicia terra, sulphur iodatum, thuja occidentalis;* 10×.

Immune Boost: *apis mellifica, borax veneta, cantharis vesicatoria, cinnabaris, echinacea angustifolia, galium aparine, hepar sulphuris calcareum, lachesis muta, mercurius corrosives, nitric acidum, pituitarum posterium, sulphur iodatum, thuja occidentalis, thymus serpyllum;* 10×.

Joint and Muscle Pain: *argentum nitricum, arnica Montana, arsenicum album, belladonna, bryonia alba, dulcamara, echinacea angustifolia, hepar sulphuris calcareum, influenzinum, lachesis muta, mercurius vivus, phytolacca decandra, pulsatilla nigricans, pyrogenium, rhus toxicodendron, thuja occidentalis;* 10×.

Skin Care: *antimonium tartaricum, asterias rubens, ferrum metallicum, hepar sulphuris calcareum, kali bromatum, natrum muriaticum, sanguinaria Canadensis, selenium, sepia succus, silicea terra, sulphur iodatum, thuja occidentalis;* 10×.

Stress and Anxiety: *aconitum napellus, apis mellifica, arnica Montana, arsenicum album, belladonna, bellis perennis, bryonia alba, calendula officinalis, chamomilla, cistus Canadensis, ferrum phosphoricum, Iristaminum muriaticum, hypericum perforatum, ignatia amara, impatiens glandulifera flos, ornithogalum umbellatum, passiflora incarnate, phosphorus, prunus cerasifera fibs, rhus toxicodendron, sulphur iodatum, symphytum officinale, veratrum album;* 10×.

Detoxifier: *hepar suis* (porcine liver organo); 12×. *benzoicum acidum, berberis vulgaris, bryonia alba, cantharis vesicatoria, ceanothus americanus, chelidonium majus, china officinalis, chionanthus virginica, dioscorea villosa, dolichos pruriens, iris versicolor, nux vomica, ptelea trifoliate, taraxacum officinale* 10×. *carduus benedictus, carduus marianus, cynara scolymos, juniperus communis, solidago virgaurea, taraxacum officinale;* 3×.

In other embodiments of the disclosure, the following compositions of homeopathic active ingredients may be utilized for the physiological conditions and applications correspondingly identified below.

Low-Energy, Mild Stress and Weakness:

Adrenalinum 15×, Aloe 15×, Arsenicum alb. 15×, Baptisia 15×, Berber. aqui. 15×, Berber. vulg. 15×, Bryonia 15×, Chelidonium majus 15×, Crotalus horridus 15×, Digitalis 15×, Ferrum metallicum 15×, Glonoinum 15×, Glycyrrhiza glabra 15×, Hydrocotyle 15×, Iodium 15×, Iris versicolor 15×, Lachesis 15×, Lycopodium 15×, Nat. mur. 15×, Nux vom. 15×, Rhus toxicodendron 15×, Ruta 15×, Thuja occ. 15×, Thyroidinum 15×, Echinacea 3×, Lappa 3×, Solidago 3×, Taraxacum 3×.

Symptoms Associated with Tobacco Use, e.g., Anxiety, Cravings, Irritability, Respiratory Conditions, and Abstinence-Mediated Stress:

Arsenicum alb. 15×, Benzoicum acidum 15×, Berber. vulg 15×, Bryonia 15×, Caladium seguinum 15×, Cantharis 15×, Ceanothus 15×, Chelidonium majus 15×, Chionanthus virginica 15×, Cinchona 15×, Daphne indica 15×, Ignatia 15×, Iris versicolor 15×, Lycopodium 15×, Nicotinum 15×, Nux vom. 15×, Rhus toxicodendron 15×, Scutellaria laterifolia 15×, Tabacum 15×, Echinacea 3×, Taraxacum 3×, Valeriana 3×.

Muscle Discomfort Such as Bruising, Pain, Soreness, Stiffness, Spasms, and Weakness:

Aconitum nap. 15×, Antimon. tart. 15×, Arg. nit. 15×, Arnica 15×, Bryona 15×, Chamomilla 15×, Chelidonium majus 15×, Cimicifuga 15×, Eupatorium perf. 15×, Hypericum 15×, Nux vom. 15×, Rhus toxicodendron 15×, Ruta 15×, Sarcolacticum ac. 15×, Stramonium 15×, Strychnium 15×, Chamomilla 3×, Phytolacca 3×, Ruta 3×, Symphytum 3×.

Symptoms Associated with Stress and Tension, e.g., Worry, Frustration, Emotional Sensitivity, and Feeling of being Mentally and Physically Drained:

Aconitum nap. 15×, Arg. nit. 15×, Aur. met. 15×, Baptisia 15×, Bryonia 15×, Chelidonium majus 15×, Cimicifuga 15×, Conium 15×, Gelsemium 15×, Ignatia 15×, Kali carb. 15×, Lachesis 15×, Lilum 15×, Lycopodium 15×, Nat. carb. 15×, Nat. mur. 15×, Phosphoricum ac. 15×, Phosphorus 15×, Picricum ac. 15×, Plumb. met. 15×, Sepia 15×, Staphysag. 15×, Stramonium 15×, Thuja occ. 15×, Zinc. met. 15×, Chamomilla 3×, Hypericum 3×, Valeriana 3×.

Symptoms Associated with Appetite Control, e.g., Overeating, Cravings, Fatigue, and Emotional Discomfort:

Anacardium orientale 15×, Antimon. crud. 15×, Arg. nit. 15×, Berber. vulg. 15×, Bryonia 15×, Chelidonium majus 15×, Digitalis 15×, Graphites 15×, Humulus 15×, Iris versicolor 15×, Kali carb. 15×, Lycopodium 15×, Nat. carb. 15×, Nat. sulphuricum 15×, Nux vom. 15×, Pulsatilla 15×, Rhus toxicodendron 15×, Scutellaria laterifolia 15×, Sepia 15×, Stramonium 15×, Chamomilla 3×, Passiflora 3×, Valeriana 3×.

Liver and Kidney Functions, and Symptoms Associated with Toxicity e.g., Fatigue, Headaches, and Sluggish Elimination:

Uricum acidum 15×, Benzoicum acidum 10×, Berber. vulg. 10×, Bryonia 10×, Cantharis 10×, Carduus benedictus 10×, Ceanothus 10×, Chelidonium majus 10×, Chionanthus virginica 10×, Cinchona 10×, Dioscorea 10×, Dolichos 10×, Iris versicolor 10×, Juniperus com. 10×, Nux vom. 10×, Ptelea 10×, Taraxacum 10×, Carduus mar. 3×, Cynara scolymus 3×, Solidago 3×, Taraxacum 3×.

In the foregoing listings of homeopathic ingredients and associated conditions/applications for which such homeopathic agents are utilized, there is indication of the potency of the ingredients that is utilized for treatment of such condition, e.g., 3×, 10×, 12×, and 15×.

Homeopathic ingredients are prepared by a process of "potentization," involving serial dilution and "succussion" (vigorous shaking) in an aqueous medium. The potency of the homeopathic remedy is described by the 2-part number and letter designation. The numeric part of the letter and number designation indicates the number of times the source substance has been homeopathically diluted and succussed. The letter portion of the number and letter designation indicates the dilution rate. For example, in the potency 12×, the source material has been homeopathically diluted and succussed twelve times and the letter "X" represents Roman numeral 10, a dilution rate of 1/10, or, stated alternatively, 1:10 dilution ratio. A dilution rate of 1/10 is very slow, while a dilution rate of 1/50,000, designated LM, is a fast dilution rate.

Homeopathic ingredients are diluted according to a decimal scale, utilizing an aqueous medium. For example, a dilution factor of 1:10 means that one part of the mother tincture starting material is diluted in 9 parts of the aqueous medium. Ten succussions are carried out between each dilution phase.

An illustrative dilution and succussion dilution process may include the following steps:

Step 1: One part of the mother tincture starting material is diluted in 9 parts of aqueous medium;

Step 2: The diluted liquid is then succussed 10 times in its bottle, e.g., by firmly hitting the bottle's base against a firm but resistive surface, or by automated shaking providing an equivalent liquid condition, so that the resulting liquid has a 1× potency the "1" referring to the first stage of dilution and the Roman numeral "X" referring to the 1:10 dilution ratio;

Step 3: One part of the 1× potency material is next diluted in 9 parts of aqueous medium and succussed 10 times to produce a 2× homeopathic material; and Step 4: The serial potentization process of dilution and succussion is repeated for a number of times that produces a desired potency of the homeopathic ingredient.

In instances in which the aqueous medium is a mixture of alcohol and water, the concentration of alcohol may be on the order of 10-30% of the total weight of the aqueous medium (wt/wt %). Dilution mixing with the aqueous medium and succussion is carried out to achieve any desired potencies, such as 3×, 9×, 10×, 11×, 12×, 14×, 15×, or 16×. It will be recognized that the homeopathic compositions used in the dried homeopathic composition-coated sucrose or sucrose/starch particles of the present disclosure can be of any suitable type, and may be varied in respect of the potency of individual active ingredients.

Once the homeopathic ingredient has been prepared, it can be stored in suitable containers until used to manufacture the drinking water formulation. The active ingredients may for example be provided in a high alcohol liquid solution containing the homeopathic ingredients, as the homeopathic composition.

In the drinking water formulation manufacturing operation, the water to be utilized in the drinking water formulation may be subjected to pre-filtration (mechanical filtration) to remove sediment and particles, softening treatment to remove hardness-causing minerals, and carbon filtration to remove objectionable taste and odor components as well as any organic chemicals that may be present. These steps may be followed by reverse osmosis, e.g., to remove 95%+ of dissolved solids in the liquid after the earlier treatments and then demineralization to remove any residual minerals, bringing the water to zero parts per million (ppm) total dissolved solids. The liquid after such treatment may be subjected to ultraviolet (UV) purification, to ensure that the water remains virtually free of microbes.

The production process may include continuous recirculation and ozone or oxygen injection to control microbial growth, thereby avoiding undesirable byproducts that are otherwise associated with chlorination treatment of the water. Such purification may be carried out to effect a residual oxygen component in the liquid for ensuring freshness in subsequent use. Final bacteria filtration may be carried out before bottling.

Bottling, as used herein, refers to the process of introducing homeopathic drinking water formulations of the disclosure to suitable containers for subsequent consumer use. The beverage container used for bottling may be a bottle or a can that is sealed subsequent to introduction of the drinking water formulation thereto. For example, the beverage container may be of a size to hold 6, 8, 10, 12, 14, 16 or more ounces of the drinking water formulation. In one embodiment, the beverage container contains 6.9 fluid ounces of water. In other embodiments, the amount of water may be in a range of from 200 to 1000 mL of water, or more.

The drinking water formulation manufacturing operation may be carried out to introduce to purified water one or more homeopathic ingredients, prepared as previously described, to provide a homeopathic drinking water formulation.

Homeopathic drinks of the present disclosure may be made using core particles formed of sucrose, or core particles formed of sucrose/maize starch, which are coated with the homeopathic composition containing the homeopathic active ingredients and volatile liquid (water and/or alcohol) as components. The homeopathic solution then can be applied to the core particles in any suitable manner, such as spraying, misting, vapor contacting, or other application modality, so that the active homeopathic ingredients are coated on the core particles. The resulting homeopathic solution-coated core particles then are dried to release the volatile liquid and produce homeopathic composition-coated core particles.

The homeopathic ingredient(s) may be added at any suitable concentration. In some embodiments, homeopathic ingredient(s) may be added at concentrations that are so low that the homeopathic active ingredient(s) are substantially undetectable. In other embodiments, the homeopathic ingredient(s) may be added at a concentration of from about 0.05% to 10% by weight, based on total weight of the drinking water formulation. It will be appreciated that the homeopathic ingredients may be employed in any suitable range of concentration, from the aforementioned undetectable levels up to significant amounts by weight, based on total weight of the homeopathic drinking water formulation.

In various embodiments, the homeopathic active ingredients may be provided in a high alcohol liquid solution containing the homeopathic composition, with the high alcohol liquid solution of the homeopathic ingredients being applied to the above-described core particles and then dried to provide the core particles coated with homeopathic active ingredients. In one embodiment, the high alcohol liquid solution of homeopathic ingredients is applied to the core pellets at a ratio of 1 milliliter of such solution for each 90.8 g weight of core particles.

Such homeopathic composition-coated core particles then can be blended with water under general shaking or agitation to effect dissolution or dispersion thereof in the water, to form the homeopathic water drink for point of use consumption. Alternatively, the homeopathic composition-coated core particles can be blended with water to form the homeopathic water drink, followed by bottling of the homeopathic water drink, for subsequent consumption.

In various embodiments of the present disclosure, the homeopathic composition-coated core particles are packaged for subsequent use in a compartment of a dispensing cap, or otherwise in a packet, sachet, or other container or packaging, from which the homeopathic composition-coated core particles can be introduced to water to constitute the homeopathic water drink at the time of consumption.

In a specific embodiment, an amount of ~1 g of the dried homeopathic composition-coated core particles is packaged in a dispensing cap to enable actuated dispensing of such particles into aqueous medium at the time of make-up of the homeopathic water drink for consumption. The dispensing cap can be of any suitable type that when secured to a bottle or other container of water, preferably purified water, can be actuated to release the homeopathic composition-coated core particles into the water. The bottle, capped with the dispensing cap, can then be shaken by the user to effect rapid dissolution or dispersion of the core particles and homeopathic composition in the liquid to form the drink for consumption. The bottle can then be uncapped to enable such consumption of the homeopathic drink.

The homeopathic composition-coated core particles in one embodiment are formed using core particles of 100% beet sucrose, 500 μm to 2000 μm in diameter. In one embodiment, 1 g of the core particles contains 400-600 particles. In another embodiment, 1 g of the core particles comprises 470-530 particles. The core particles in another embodiment are formed of a sucrose/maize starch composition, e.g., of 85.7% beet sucrose, and 14.3% of maize starch, and may be in a range of from 700 to 900 μm in diameter. In a specific embodiment, such sucrose/maize starch particles have a diameter in a range of from 710 to 850 μm.

Thus, the homeopathic water formulations of the disclosure in various embodiments may consist of water, active homeopathic ingredients, and sucrose. In other embodiments, the homeopathic water formulations may consist of water, active homeopathic ingredients, sucrose, and cornstarch. Such homeopathic water formulations are advantageously made up at the time of consumption, to obviate the need for any preservatives or other excipients.

Still other homeopathic water formulations may be pre-mixed, and provided to consumers in bottled or packaged form, and may consist of the foregoing constituents (water, active homeopathic ingredients, and sucrose; or alternatively, water, active homeopathic ingredients, sucrose, and cornstarch) and one or more preservative ingredient(s).

The homeopathic water drink in still other embodiments of the disclosure contains at least one additive selected from among (i) sodium benzoate, (ii) citric acid and potassium benzoate, (iii) citric acid and potassium sorbate, and (iv) effervescence agent(s). These additives may be employed at any suitable concentrations that do not preclude the homeopathic utility or general benefit of the drinking water formulation. Typically, such additives can be incorporated in the drinking water formulation at a concentration of from about 0.05% to 4% by weight, based on total weight of the formulation.

In various embodiments, the use of such additives can be employed to enable homeopathic water formulations to be prepared without the need of alcohol in the aqueous medium that is used for dilution and succussion of the homeopathic ingredient. As a result, alcohol-free water formulations may be made without the need of alcohol in the dilution/succussion aqueous medium.

In one illustrative formulation utilizing the aforementioned additives, the drinking water may contain homeopathic ingredient(s) in liquid or solid form, e.g., in an amount of 0.5 milliliter to each 16 ounces of water in the formulation. Sodium benzoate may for example be added at a concentration of 0.5 weight percent, based on the total weight of the formulation. Alternatively, in place of sodium benzoate, 0.5% by weight of citric acid and 1% by weight of potassium benzoate may be used, or as a still further alternative, a mixture of 0.5% by weight of citric acid and 1% by weight of potassium sorbate may be employed.

The drinking water formulation may additionally, or alternatively, contain an effervescence agent or agents, to provide an effervescent water formulation for consumption by a consumer.

The effervescence agent may include any suitable effervescing agent, such as a mixture of acids or acid salts and carbonate ingredients that react to release carbon dioxide in the presence of water. For example, suitable acids and acid salts may include citric acid, tartaric acid, malic acid, or corresponding acid anhydride. Carbonates may include sodium carbonate, potassium carbonate or any other suitable alkali metal carbonate or hydrogen carbonate that is useful in reaction with the acid component to release carbon dioxide in the presence of water.

The respective effervescence ingredients may be in the form of powders or solids that are present with one another in a dry mixture that then is added to the drinking water formulation to produce the effervescent water product.

In one embodiment, the effervescent agents are sequestered in a portion of the beverage container, such as in a compartment in a cap of the container, and are released by the user when readying the beverage article for consumption, so that the drinking water formulation is rendered effervescent in character.

In like manner, the homeopathic ingredients, e.g., coated on the above-described sucrose or sucrose/starch particles, may be packaged separately from the water in the beverage container to constitute the water formulation at the time of use, by releasing the homeopathic ingredients for mixing with the water and any additional components of the formulation.

In further embodiments, all of the homeopathic ingredients may be mixed with one another, e.g., in a solid and/or liquid form, with the mixture sequestered from the aqueous component of the drinking water formulation in the container so that it can be contacted with the water at the time of use for consumption.

Accordingly, the disclosure contemplates homeopathic ingredients and/or other formulation ingredients in powdered or dry form or alternatively in liquid form, that are mixed with water at the point of use, by means of an integrated package containing water in a volume or compartment of the beverage article that is separated from the other ingredients.

The homeopathic water formulations of the disclosure may be utilized as a hydration medium that additionally is useful in treatment of ailments and conditions for which homeopathic remedies are effective, e.g., stress, fatigue, headaches, heartburn, etc.

The drinking water formulations of the present disclosure may variously comprise, consist or consist essentially of specified ingredients herein disclosed. Other ingredients may be incorporated in such formulations, e.g., vitamins, minerals, probiotics, dietary additives, nutriceuticals, and/or any other active or inactive ingredients that are usefully incorporated in the drinking water formulation for ultimate use.

The disclosure contemplates a beverage article, comprising a beverage container, and a drinking water formulation of the disclosure in such container. As mentioned, the beverage container may be adapted to release the homeopathic ingredients by user action, in readying the beverage article for consumption.

The disclosure contemplates various methods of making a homeopathic drinking water formulation, beginning with the provision of a mother tincture of a homeopathic ingredient that is diluted to form a first mixture. The first mixture is succussed. A final mixture is prepared from the first mixture, by carrying out dilution (and subsequent succussion) steps for a number of times n, wherein n is zero (in which case the first mixture is the final mixture) or a whole number integer.

In such method, at least one additive may be added to at least one of the mother tincture, first mixture (when different from the final mixture) and final mixture. The additive may for example be selected from among (i) sodium benzoate, (ii) citric acid and potassium benzoate, (iii) citric acid and potassium sorbate, and (iv) effervescence agent(s). The effervescence agents when present may be added at the time of bottling, or may be released from a separate compartment into the water, to produce effervescing action. In like manner, the other additive composition ingredients may be arranged to be added into the water at the point of use.

The disclosure further contemplates dry mixtures of the homeopathic ingredients and effervescence agents, as a powder composition that is released into the water of the formulation, and that by effervescent action mixes the water volume to disperse and solubilize the homeopathic ingredient(s).

The dilution of mother tincture compositions in the practice of the present disclosure can be carried out in any suitable manner, and may for example, involve the following designations and dilution rates as set forth in Table 1 below.

TABLE 1

| Designation | Dilution Rate |
|---|---|
| X | 1/10 |
| C | 1/100 |
| M | 1/1000 |
| LM | 1/50,000 |

FIG. 1 is a schematic representation of a process of preparing a homeopathic composition of a mother tincture starting material, involving successive dilution and sucession steps, to achieve homeopathic potentization of a homeopathic component, with successive steps producing 1×, 2×, and 3× potencies. In this illustrative preparation, the starting material is mixed with an aqueous medium in an amount of 1 part mother tincture to 9 parts water and alcohol mixture. In instances in which non-alcoholic homeopathic water formulations are prepared, the aqueous medium contains no alcohol.

FIG. 2 is a perspective view of a beverage article according to one embodiment of the disclosure.

The beverage article 10 shown in FIG. 2 includes a beverage container 12 defining an interior volume 16 holding a volume 18 of the homeopathic water formulation. The container may as shown comprise a conventional bottle, or alternatively a can or other container. The container shown includes a sleeve 14 of plastic, cellulosic or other suitable material, containing labeling indicia thereon. Such labeling indicia may for example include a listing of the homeopathic active ingredients, directions for use, etc.

The beverage article 10 in the FIG. 2 embodiment includes a cap 20 having suitable threading or other engagement structure for cooperative sealing of the bottle, in a conventional manner.

The cap in this embodiment provides for retention of effervescent agents 30 in a compartment of the cap, as shown in greater detail in FIG. 3, which is a perspective enlarged view of the structure. The cap may include a pull ring 24 as shown, connected to a length of wire 36 that is embedded in a foil barrier element 32 (see FIG. 3). This arrangement maintains the effervescence agents 30 in the compartment of the cap until the point of use, at which time the user pulls the pull ring 24 in the direction shown by arrow A This action causes the wire embedded in the foil barrier element 32 to be withdrawn from the barrier element and the cap, to thereby tear away a circular opening in the barrier element to allow the effervescence agents to gravitationally fall into the underlying liquid 18. The effervescence agents upon contact with such water volume undergo reaction to produce carbon dioxide for carbonation of liquid in the beverage container. The vessel upon subsequent removal of the cap is carbonated in character and ready for consumption.

In like manner, the homeopathic ingredient may be sequestered from the liquid in the cap compartment, and the homeopathic ingredient may then by user action of the dispensing cap be released from the cap and mixed into the water to form the homeopathic water formulation.

The cap 20, instead of containing effervescence agents 30, may contain only homeopathic composition-coated sucrose or sucrose/starch pellets, without any effervescence agents or any other agents or ingredients, so that the cap when actuated releases the homeopathic composition-coated pellets into the water in container 12 to provide the homeopathic water drink for a consumer.

Caps useful for sequestering the various solid and/or liquid ingredients from the water in the beverage container include those described in U.S. Pat. Nos. 6,974,024 and 7,070,046 and U.S. Patent Application Publications 2006/0108314, 2007/0119727, 2005/0150902 and 2008/0142473, all in the name of Young Kook Cho.

The homeopathic formulations of the present disclosure may be presented for use on particles of small size, e.g., core particles that may be in a size range of from 400 to 2000 micrometers, to which a homeopathic composition of homeopathic ingredients in an alcohol solution has been applied, and subsequently dried to remove alcohol and water, yielding homeopathic composition-coated particles. The core particles can be formed of sucrose, or of a sucrose/starch blend, as hereinabove described, or such homeopathic composition-coated particles can be formed using any other suitable core material that is compatible with the homeopathic composition, and that is rapidly dissolving or dispersing in water or other aqueous medium, to place the homeopathic active ingredients in aqueous medium.

In some embodiments, the core particles are formed of 100% beet sucrose, and have a diameter, or major dimension, that is in a range of from 1000 to 1600 micrometers, with approximately 470 to 530 core particles per gram. In other embodiments, the particles are formed of 85.7% beet sucrose and 14.3% of maize starch, and have a diameter in a range of from 710 to 850 micrometers.

Core particles of such type, when coated with the homeopathic composition, may be packaged for point-of-use mixing with water, e.g., by release from a dispensing cap storing same into a bottle or other container coupled with the cap, at a ratio of 1 gram of homeopathic composition-coated mini-pellets to 200 to 1000 mL of water, or more, depending on the specific homeopathic composition employed, and the specific character of the water or other aqueous medium with which the homeopathic composition-coated mini-pellets are blended to form the homeopathic drink.

Alternatively, the homeopathic composition-coated mini-pellets may be premixed in a homeopathic water drink, e.g., being bottled with preservative(s) and optionally other ingredients, as desired.

In various embodiments, the homeopathic composition-coated pellets of the disclosure consist of only the beet sucrose or beet sucrose/starch pellets and the homeopathic active ingredients coated thereon, and the corresponding homeopathic drink consists only of water in which such homeopathic composition-coated pellets have been dissolved or suspended.

In other embodiments, in which the homeopathic composition-coated pellets of the disclosure have been dissolved or suspended in water, as a ready-to-consume drink that is bottled and sold in bottled form, the drink may additionally include a preservative, so that the drink consists of only water, dissolved or suspended homeopathic composition-coated pellets as described above, and the preservative.

The homeopathic composition-coated pellets are advantageously packaged in dispensing caps that can be manually actuated at the time of use, to dispense the homeopathic composition-coated pellets into water, e.g., into a bottle filled with water to which the dispensing cap has been secured, so that upon dispensing, optionally with shaking of the capped bottle to effect dissolution or dispersion of the pellets in the water, the homeopathic drink is provided.

A multiplicity of such dispensing caps, each loaded with homeopathic composition-coated pellets of a same homeopathic composition, or with different caps being loaded with homeopathic composition-coated pellets of different homeopathic compositions, may be packaged together and sold as a unitary product. The caps as thus packaged can be of a standard cap size fitting a consumer water bottle, or alternatively the multiple caps can be packaged with a reusable water bottle that can be filled by a user at the point of use with water, e.g., tap water, purified water, or other aqueous medium.

FIG. 4 is a front elevation view of a beverage article according to another embodiment of the disclosure. The beverage article includes a container 50 adapted to contain a predetermined amount of water, e.g., purified water, in an amount of 500 mL. The container 50 is of cylindrical shape with a threaded neck portion terminating in an upper opening. The threaded neck portion is complementarily threaded for engagement with the cap 60, as illustrated.

The cap 60 comprises an elongate cylindrical housing extending upwardly from the threaded lower collar portion thereof. Such elongate cylindrical housing contains a charge or "dose" of the homeopathic pellets, in which each pellet may comprise a sucrose-based core on which has been coated a homeopathic composition, as previously described. Such dose of the pellets is retained in the elongate cylindrical housing of the cap, and at the time of use is released from the cylindrical housing to drop into the underlying water, by exerting downward manual pressure on the top surface of the cap, e.g., by pressing on the top of the cap with a thumb or finger. Once the homeopathic pellets are released, they drop into and dissolve or disperse in the water in the container 50, to form the homeopathic aqueous drink.

The container itself can be of any suitable construction, and can for example be formed of a bisphenol-A-free material, such as a BPA-free polyethylene terephthalate material.

The charge of homeopathic pellets can be retained in the elongate cylindrical housing of the cap by a liner that is broken when manual downward pressure is exerted on the top surface of the cap. In such arrangement, downward pressure is exerted on the charge of homeopathic pellets in the cap so that they press against and burst the liner retaining the homeopathic pellets in the cap, to thereby release the pellets into the water. For such purpose, the cap may be fabricated with a flexible, deformable top structure. Other release structures and elements may be employed, whereby the cap can be manually actuated by a user, to release the charge of homeopathic composition-coated core particles into the underlying water after the bottle has been filled with an appropriate amount of water for such purpose.

The container may be provided in an empty state in the first instance so that it can be filled with a suitable quantity of water, e.g., purified water, at the time of use. Alternatively, the container may be provided in a filled state, with for example a volume in a range of from 200 to 1000 mL of water, with a cap containing a suitable amount of the pellets coated with the homeopathic composition, e.g., an amount in a range of from 0.5 to 4 grams of the homeopathic composition-coated pellets.

The disclosure in one embodiment contemplates a homeopathic drink product, comprising a reusable container that is packaged with one or more storage caps that are adapted for coupling with the reusable container, e.g., by complementary threading of matably engageable structure on the container neck at the open mouth of the container, and the interior sidewall surface of the storage cap. Each storage cap in such package contains a quantity of homeopathic composition-coated core particles, and the homeopathic composition is the same in each of the storage caps.

Another embodiment of the disclosure relates to a homeopathic drink product, comprising a reusable container packaged with multiple storage caps that are adapted for coupling with the reusable container, e.g., by complementary threading of matably engageable structure on the container neck at the open mouth of the container, and the interior sidewall surface of the storage cap. Each storage cap in such packaged product contains a different homeopathic composition on the homeopathic composition-coated particles, to provide a variety of different homeopathic drinks in a single package, so that each of the storage caps containing a different homeopathic composition on the homeopathic composition-coated particles may be used with the reusable container on different occasions, each employing a different homeopathic composition in water that is filled in the container for such purpose.

It will be recognized that the compositions, packages, and products of the present disclosure may be made and utilized in a variety of different forms, as appropriate to the specific formulation(s) and presentational requirements of a given application.

The features and advantages of the disclosure are further illustrated by the following non-limiting examples.

Example 1

Boost Formulation

In this example, a homeopathic composition formulated for symptoms associated with low energy, mild stress, and weakness is made up, as an alcohol-preserved liquid solution with the following active ingredients: *Adrenalinum* 15×, *Aloe* 15×, *Arsenicum alb.* 15×, *Baptisia* 15×, *Berber. aqui.* 15×, *Berber. vulg.* 15×, *Bryonia* 15×, *Chelidonium majus* 15×, *Crotalus horridus* 15×, *Digitalis* 15×, *Ferrum metallicum* 15×, *Glonoinum* 15×, *Glycyrrhiza glabra* 15×, *Hydrocotyle* 15×, *Iodium* 15×, *Iris versicolor* 15×, *Lachesis* 15×, *Lycopodium* 15×, *Nat. mur.* 15×, *Nux vom.* 15×, *Rhus toxicodendron* 15×, *Ruta* 15×, *Thuja* occ. 15×, *Thyroidinum* 15×, *Echinacea* 3×, *Lappa* 3×, *Solidago* 3×, *Taraxacum* 3×.

Pellets are provided as support particles for the homeopathic composition. The pellets have a composition of 85.7% beet sucrose and 14.3% cornstarch, and a particle diameter in a range of from 710 to 850 micrometers. A batch of such pellets, weighing 1362 grams, is then contacted with 15 milliliters (mL) of the above-described alcohol liquid solution of the homeopathic ingredients, to coat the pellets with the solution. The solution then dries to yield the pellets coated with the homeopathic composition.

One gram of the homeopathic composition-coated pellets then is introduced to the storage compartment of a finger-pressure-activated storage cap, of a type as shown and described in connection with the FIG. 4 beverage article embodiment, in which manual pressure exerted on a top end of the cap releases the pellets into the water in the bottle of such beverage article. The beverage article may be provided in the first instance with the bottle empty of water, so that a consumer can fill the bottle with water, e.g., a quantity such as 17 fluid ounces of water. After water fill of the bottle, the user can then engage the pellets-containing cap with the bottle and apply manual pressure of a finger on the top of the pressure-actuatable storage cap to release the charge of pellets into the water in the bottle. The capped bottle can then be shaken to accelerate the dissolution of the pellets in the water to form the homeopathic water for subsequent drinking by the consumer.

Example 2

NoBacco Formulation

The homeopathic composition in this example is formulated for symptoms associated with tobacco use, such as anxiety, cravings, irritability, respiratory conditions and stress caused by abstinence. The composition is made up as an alcohol-preserved liquid solution with the following active ingredients: *Arsenicum alb.* 15×, *Benzoicum acidum* 15×, *Berber. vulg* 15×, *Bryonia* 15×, *Caladium seguinum* 15×, *Cantharis* 15×, *Ceanothus* 15×, *Chelidonium majus* 15×, *Chionanthus virginica* 15×, *Cinchona* 15×, *Daphne indica* 15×, *Ignatia* 15×, *Iris versicolor* 15×, *Lycopodium* 15×, *Nicotinum* 15×, *Nux vom.* 15×, *Rhus toxicodendron* 15×, *Scutellaria laterifolia* 15×, *Tabacum* 15×, *Echinacea* 3×, *Taraxacum* 3×, *Valeriana* 3×.

Pellets are provided as support particles for the homeopathic composition. The pellets have a composition of 85.7% beet sucrose and 14.3% cornstarch, and a particle diameter in a range of from 710 to 850 micrometers. A batch of such pellets, weighing 1362 grams, is then contacted with 15 milliliters (mL) of the above-described alcohol liquid solution of the homeopathic ingredients, to coat the pellets with the solution. The solution then dries to yield the pellets coated with the homeopathic composition.

One gram of the homeopathic composition-coated pellets then is introduced to the storage compartment of a finger-pressure-activated storage cap, of a type as shown and described in connection with the FIG. 4 beverage article embodiment, in which manual pressure exerted on a top end of the cap releases the pellets into the water in the bottle of such beverage article. The beverage article may be provided in the first instance with the bottle empty of water, so that a consumer can fill the bottle with water, e.g., a quantity such as 17 fluid ounces of water. After water fill of the bottle, the user can then engage the pellets-containing cap with the bottle and apply manual pressure of a finger on the top of the pressure-actuatable storage cap to release the charge of pellets into the water in the bottle. The capped bottle can then be shaken to accelerate the dissolution of the pellets in the water to form the homeopathic water for subsequent drinking by the consumer.

Example 3

Ease Formulation

The homeopathic composition in this example is formulated for symptoms associated with muscle discomfort such as bruising, pain, soreness, stiffness, spasms and weakness. The composition is made up as an alcohol-preserved liquid solution with the following active ingredients: *Aconitum nap.* 15×, *Antimon. tart.* 15×, *Arg. nit.* 15×, *Arnica* 15×, *Bryona* 15×, *Chamomilla* 15×, *Chelidonium majus* 15×, *Cimicifuga* 15×, *Eupatorium perf.* 15×, *Hypericum* 15×, *Nux vom.* 15×, *Rhus toxicodendron* 15×, *Ruta* 15×, *Sarcolacticum ac.* 15×, *Stramonium* 15×, *Strychnium* 15×, *Chamomilla* 3×, *Phytolacca* 3×, *Ruta* 3×, *Symphytum* 3×.

Pellets are provided as support particles for the homeopathic composition. The pellets have a composition of 85.7% beet sucrose and 14.3% cornstarch, and a particle diameter in a range of from 710 to 850 micrometers. A batch of such pellets, weighing 1362 grams, is then contacted with 15 milliliters (mL) of the above-described alcohol liquid solution of the homeopathic ingredients, to coat the pellets with the solution. The solution then dries to yield the pellets coated with the homeopathic composition.

One gram of the homeopathic composition-coated pellets then is introduced to the storage compartment of a finger-pressure-activated storage cap, of a type as shown and described in connection with the FIG. 4 beverage article embodiment, in which manual pressure exerted on a top end of the cap releases the pellets into the water in the bottle of such beverage article. The beverage article may be provided in the first instance with the bottle empty of water, so that a consumer can fill the bottle with water, e.g., a quantity such as 17 fluid ounces of water. After water fill of the bottle, the user can then engage the pellets-containing cap with the bottle and apply manual pressure of a finger on the top of the pressure-actuatable storage cap to release the charge of pellets into the water in the bottle. The capped bottle can then be shaken to accelerate the dissolution of the pellets in the water to form the homeopathic water for subsequent drinking by the consumer.

Example 4

Calm Formulation

The homeopathic composition in this example is formulated for symptoms associated with stress and tension such as worry, frustration, emotional sensitivity and the feeling of being mentally and physically drained. The composition is made up as an alcohol-preserved liquid solution with the following active ingredients: *Aconitum nap.* 15×, *Arg. nit.* 15×, *Aur. met.* 15×, *Baptisia* 15×, *Bryonia* 15×, *Chelidonium majus* 15×, *Cimicifuga* 15×, *Conium* 15×, *Gelsemium* 15×, *Ignatia* 15×, *Kali carb.* 15×, *Lachesis* 15×, *Lilum* 15×, *Lycopodium* 15×, *Nat. carb.* 15×, *Nat. mur.* 15×, *Phosphoricum ac.* 15×, *Phosphorus* 15×, *Picricum ac.* 15×, *Plumb. met.* 15×, *Sepia* 15×, *Staphysag.* 15×, *Stramonium* 15×, *Thuja occ.* 15×, *Zinc. met.* 15×, *Chamomilla* 3×, *Hypericum* 3×, *Valeriana* 3×.

Pellets are provided as support particles for the homeopathic composition. The pellets have a composition of 85.7% beet sucrose and 14.3% cornstarch, and a particle diameter in a range of from 710 to 850 micrometers. A batch of such pellets, weighing 1362 grams, is then contacted with 15 milliliters (mL) of the above-described alcohol liquid solution of the homeopathic ingredients, to coat the pellets with the solution. The solution then dries to yield the pellets coated with the homeopathic composition.

One gram of the homeopathic composition-coated pellets then is introduced to the storage compartment of a finger-pressure-activated storage cap, of a type as shown and described in connection with the FIG. 4 beverage article embodiment, in which manual pressure exerted on a top end of the cap releases the pellets into the water in the bottle of such beverage article. The beverage article may be provided in the first instance with the bottle empty of water, so that a consumer can fill the bottle with water, e.g., a quantity such as 17 fluid ounces of water. After water fill of the bottle, the user can then engage the pellets-containing cap with the bottle and apply manual pressure of a finger on the top of the pressure-actuatable storage cap to release the charge of pellets into the water in the bottle. The capped bottle can then be shaken to accelerate the dissolution of the pellets in the water to form the homeopathic water for subsequent drinking by the consumer.

Example 5

Cleanse Formulation

In this example, the homeopathic composition is formulated for liver and kidney functions and for symptoms associated with toxicity such as fatigue, headaches, and sluggish elimination. The composition is made up as an alcohol-preserved liquid solution with the following active ingredients: *Uricum acidum* 15×, *Benzoicum acidum* 10×, *Berber. vulg.* 10×, *Bryonia* 10×, *Cantharis* 10×, *Carduus benedictus* 10×, *Ceanothus* 10×, *Chelidonium majus* 10×, *Chionanthus virginica* 10×, *Cinchona* 10×, *Dioscorea* 10×, *Dolichos* 10×, *Iris versicolor* 10×, *Juniperus com.* 10×, *Nux vom.* 10×, *Ptelea* 10×, *Taraxacum* 10×, *Carduus mar.* 3×, *Cynara scolymus* 3×, *Solidago* 3×, *Taraxacum* 3×.

Pellets are provided as support particles for the homeopathic composition. The pellets have a composition of 85.7% beet sucrose and 14.3% cornstarch, and a particle diameter in a range of from 710 to 850 micrometers. A batch of such pellets, weighing 1362 grams, is then contacted with 15 milliliters (mL) of the above-described alcohol liquid solution of the homeopathic ingredients, to coat the pellets with the solution. The solution then dries to yield the pellets coated with the homeopathic composition.

One gram of the homeopathic composition-coated pellets then is introduced to the storage compartment of a finger-pressure-activated storage cap, of a type as shown and described in connection with the FIG. 4 beverage article embodiment, in which manual pressure exerted on a top end of the cap releases the pellets into the water in the bottle of such beverage article. The beverage article may be provided in the first instance with the bottle empty of water, so that a consumer can fill the bottle with water, e.g., a quantity such as 17 fluid ounces of water. After water fill of the bottle, the user can then engage the pellets-containing cap with the bottle and apply manual pressure of a finger on the top of the pressure-actuatable storage cap to release the charge of pellets into the water in the bottle. The capped bottle can then be shaken to accelerate the dissolution of the pellets in the water to form the homeopathic water for subsequent drinking by the consumer.

Example 6

Control Formulation

The homeopathic formulation in this example is formulated for symptoms associated with appetite control such as overeating, cravings, fatigue, and emotional discomfort. The composition is made up as an alcohol-preserved liquid solution with the following active ingredients: *Anacardium orientale* 15×, *Antimon. crud.* 15×, *Arg. nit.* 15×, *Berber. vulg.* 15×, *Bryonia* 15×, *Chelidonium majus* 15×, *Digitalis* 15×, *Graphites* 15×, *Humulus* 15×, *Iris versicolor* 15×, *Kali carb.* 15×, *Lycopodium* 15×, *Nat. carb.* 15×, *Nat. sulphuricum* 15×, *Nux vom.* 15×, *Pulsatilla* 15×, *Rhus toxicodendron* 15×, *Scutellaria laterifolia* 15×, *Sepia* 15×, *Stramonium* 15×, *Chamomilla* 3×, *Passiflora* 3×, *Valeriana* 3×.

Pellets are provided as support particles for the homeopathic composition. The pellets have a composition of 85.7% beet sucrose and 14.3% cornstarch, and a particle diameter in a range of from 710 to 850 micrometers. A batch of such pellets, weighing 1362 grams, is then contacted with 15 milliliters (mL) of the above-described alcohol liquid solution of the homeopathic ingredients, to coat the pellets with the solution. The solution then dries to yield the pellets coated with the homeopathic composition.

One gram of the homeopathic composition-coated pellets then is introduced to the storage compartment of a finger-pressure-activated storage cap, of a type as shown and described in connection with the FIG. 4 beverage article embodiment, in which manual pressure exerted on a top end of the cap releases the pellets into the water in the bottle of such beverage article. The beverage article may be provided in the first instance with the bottle empty of water, so that a consumer can fill the bottle with water, e.g., a quantity such as 17 fluid ounces of water. After water fill of the bottle, the user can then engage the pellets-containing cap with the bottle and apply manual pressure of a finger on the top of the pressure-actuatable storage cap to release the charge of pellets into the water in the bottle. The capped bottle can then be shaken to accelerate the dissolution of the pellets in the water to form the homeopathic water for subsequent drinking by the consumer.

Example 7

Alternative Formulations

Alternative formulations to those identified in Examples 1-6 are made up using pellets comprising core granules having a composition of 100% beet sucrose, with a size in a range of from 1000 to 1600 micrometers. One gram of such pellets contains approximately 470 to 530 granules, as coated with the homeopathic composition in the previously described manner. The pellets coated with the homeopathic compositions are packaged in the pressure-actuatable caps as previously described, with each cap containing one gram of the homeopathic composition-coated pellets.

Example 8

Pre-Mixed Formulations

Alternative formulations to those identified in Examples 1-6 are made up in a premixed form by mixing one gram of the homeopathic composition-coated pellets with 500 mL of purified water to dissolve the pellets and the homeopathic composition coated thereon, into the purified water. An effective amount of a preservative is then added to the resultant formulation, and the formulation is bottled as a premixed homeopathic drink in capped bottles, for subsequent uncapping and consumption by a user.

While the disclosure has been set out herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the invention as hereinafter claimed is intended to be broadly construed and interpreted, as including all such variations, modifications and alternative embodiments, within its spirit and scope.

What is claimed is:

1. A method of making a homeopathic drinking water formulation, comprising
    mixing an aqueous medium with an aqueously soluble or dispersible composition comprising a dry particulate homeopathic material,
    said dry particulate homeopathic material consisting of a homeopathic composition consisting of at least one active homeopathic ingredient and, optionally, an effervescence agent,
    said homeopathic composition coated on core particles comprising sucrose or a blend of sucrose and starch; and
    dissolving or dispersing the aqueously soluble or dispersible composition in the aqueous medium.

2. The method of claim 1, wherein said core particles have diameter in a range of from 400 μm to 2000 μm.

3. The method of claim 1, wherein the dry particulate homeopathic material is formed by applying the homeopathic composition in an aqueous alcohol solution to the core particles and drying the coated particles to remove the water and alcohol.

4. The method of claim 3, wherein the homeopathic composition in an aqueous alcohol solution is applied to the core particles by spraying, misting or vapor contacting.

5. The method of claim 1, wherein the aqueously soluble or dispersible composition is dissolved in the aqueous medium by shaking the mixture of aqueous medium and aqueously soluble or dispersible composition.

6. The method of claim 1, wherein the core particles are particles formed of sucrose.

7. The method of claim 1, wherein the core particles are particles formed of a blend of sucrose and starch.

8. The method of claim 1, wherein the aqueous medium is purified water.

9. The method of claim 1, wherein the aqueous medium is a mixture of alcohol and purified water.

10. The method of claim 1, wherein the aqueous medium comprises a preservative.

11. The method of claim 1, wherein the aqueous medium comprises one or more vitamins, minerals, probiotics, dietary additives, or nutriceuticals.

12. The method of claim 1, wherein the homeopathic composition includes an effervescence agent.

13. The method of claim 1, wherein the homeopathic composition is selected from the group consisting of:
    (a) a homeopathic composition of *Adrenalinum* 15×, *Aloe* 15×, *Arsenicum alb.* 15×, *Baptisia* 15×, *Berber. aqui.* 15×, *Berber. vulg.* 15×, *Bryonia* 15×, *Chelidonium majus* 15×, *Crotalus horridus* 15×, *Digitalis* 15×, *Ferrum metallicum* 15×, *Glonoinum* 15×, *Glycyrrhiza glabra* 15×, *Hydrocotyle* 15×, *Iodium* 15×, *Iris versicolor* 15×, *Lachesis* 15×, *Lycopodium* 15×, *Nat. mur.* 15×, *Nux* vom. 15×, *Rhus toxicodendron* 15×, *Ruta* 15×, *Thuja occ.* 15×, *Thyroidinum* 15×, *Echinacea* 3×, *Lappa* 3×, *Solidago* 3×, *Taraxacum* 3×;

(b) a homeopathic composition of *Arsenicum alb.* 15×, *Benzoicum acidum* 15×, *Berber. vulg* 15×, *Bryonia* 15×, *Caladium seguinum* 15×, *Cantharis* 15×, *Ceanothus* 15×, *Chelidonium majus* 15×, *Chionanthus virginica* 15×, *Cinchona* 15×, *Daphne indica* 15×, *Ignatia* 15×, *Iris versicolor* 15×, *Lycopodium* 15×, *Nicotinum* 15×, *Nux vom.* 15×, *Rhus toxicodendron* 15×, *Scutellaria laterifolia* 15×, *Tabacum* 15×, *Echinacea* 3×, *Taraxacum* 3×, *Valeriana* 3×;

(c) a homeopathic composition of *Aconitum nap.* 15×, *Antimon. tart.* 15×, *Arg. nit.* 15×, *Arnica* 15×, *Bryona* 15×, *Chamomilla* 15×, *Chelidonium majus* 15×, *Cimicifuga* 15×, *Eupatorium perf.* 15×, Hypericum 15×, *Nux vom.* 15×, *Rhus toxicodendron* 15×, *Ruta* 15×, *Sarcolacticum ac.* 15×, *Stramonium* 15×, *Strychnium* 15×, *Chamomilla* 3×, *Phytolacca* 3×, *Ruta* 3×, *Symphytum* 3×;

(d) a homeopathic composition of *Aconitum nap.* 15×, *Arg. nit.* 15×, *Aur. met.* 15×, *Baptisia* 15×, *Bryonia* 15×, *Chelidonium majus* 15×, *Cimicifuga* 15×, *Conium* 15×, *Gelsemium* 15×, *Ignatia* 15×, Kali carb. 15×, *Lachesis* 15×, *Lilum* 15×, *Lycopodium* 15×, *Nat. carb.* 15×, *Nat. mur.* 15×, *Phosphoricum ac.* 15×, *Phosphorus* 15×, *Picricum ac.* 15×, *Plumb. met.* 15×, *Sepia* 15×, *Staphysag.* 15×, *Stramonium* 15×, *Thuja occ.* 15×, *Zinc. met.* 15×, *Chamomilla* 3×, *Hypericum* 3×, *Valeriana* 3×;

(e) a homeopathic composition of *Anacardium orientale* 15×, *Antimon. crud.* 15×, *Arg. nit.* 15×, *Berber. vulg.* 15×, *Bryonia* 15×, *Chelidonium majus* 15×, *Digitalis* 15×, *Graphites* 15×, Humulus 15×, *Iris versicolor* 15×, *Kali carb.* 15×, *Lycopodium* 15×, *Nat. carb.* 15×, *Nat. sulphuricum* 15×, *Nux vom.* 15×, *Pulsatilla* 15×, *Rhus toxicodendron* 15×, *Scutellaria laterifolia* 15×, *Sepia* 15×, Stramonium 15×, *Chamomilla* 3×, *Passiflora* 3×, *Valeriana* 3×; and (f) a homeopathic composition of *Uricum acidum* 15×, *Benzoicum acidum* 10×, *Berber. vulg.* 10×, *Bryonia* 10×, *Cantharis* 10×, *Carduus benedictus* 10×, *Ceanothus* 10×, *Chelidonium majus* 10×, *Chionanthus virginica* 10×, *Cinchona* 10×, *Dioscorea* 10×, *Dolichos* 10×, *Iris versicolor* 10×, *Juniperus com.* 10×, *Nux vom.* 10×, *Ptelea* 10×, *Taraxacum* 10×, *Carduus mar.* 3×, *Cynara scolymus* 3×, *Solidago* 3×, *Taraxacum* 3×.

14. An aqueously soluble or dispersible homeopathic material consisting of a homeopathic composition consisting of at least one active homeopathic ingredient coated on core particles comprising sucrose or a blend of sucrose and starch.

15. The homeopathic material of claim 14, wherein said core particles have diameter in a range of from 400 µm to 2000 µm.

16. The homeopathic material of claim 14, wherein the core particles are particles formed of 100% beet sucrose.

17. The homeopathic material of claim 16, wherein the core particles have a diameter in a range of from 1000 to 1600 µm.

18. The homeopathic material of claim 14, wherein the core particles are particles formed of a blend of beet sucrose and maize starch.

19. The homeopathic material of claim 14, wherein the homeopathic composition is selected from the group consisting of:

(a) a homeopathic composition of *Adrenalinum* 15×, *Aloe* 15×, *Arsenicum alb.* 15×, *Baptisia* 15×, *Berber. aqui.* 15×, *Berber. vulg.* 15×, *Bryonia* 15×, *Chelidonium majus* 15×, *Crotalus horridus* 15×, Digitalis 15×, *Ferrum metallicum* 15×, *Glonoinum* 15×, *Glycyrrhiza glabra* 15×, *Hydrocotyle* 15×, *Iodium* 15×, *Iris versicolor* 15×, *Lachesis* 15×, *Lycopodium* 15×, *Nat. mur.* 15×, *Nux vom.* 15×, Rhus toxicodendron 15×, *Ruta* 15×, *Thuja occ.* 15×, *Thyroidinum* 15×, Echinacea 3×, *Lappa* 3×, *Solidago* 3×, *Taraxacum* 3×;

(b) a homeopathic composition of *Arsenicum alb.* 15×, *Benzoicum acidum* 15×, *Berber. vulg* 15×, *Bryonia* 15×, *Caladium seguinum* 15×, *Cantharis* 15×, *Ceanothus* 15×, *Chelidonium majus* 15×, *Chionanthus virginica* 15×, *Cinchona* 15×, *Daphne indica* 15×, *Ignatia* 15×, *Iris versicolor* 15×, *Lycopodium* 15×, *Nicotinum* 15×, *Nux vom.* 15×, *Rhus toxicodendron* 15×, *Scutellaria laterifolia* 15×, *Tabacum* 15×, *Echinacea* 3×, *Taraxacum* 3×, *Valeriana* 3×;

(c) a homeopathic composition of *Aconitum nap.* 15×, *Antimon. tart.* 15×, *Arg. nit.* 15×, *Arnica* 15×, *Bryona* 15×, *Chamomilla* 15×, *Chelidonium majus* 15×, *Cimicifuga* 15×, *Eupatorium pert* 15×, Hypericum 15×, *Nux vom.* 15×, *Rhus toxicodendron* 15×, *Ruta* 15×, *Sarcolacticum ac.* 15×, *Stramonium* 15×, *Strychnium* 15×, *Chamomilla* 3×, *Phytolacca* 3×, *Ruta* 3×, *Symphytum* 3×;

(d) a homeopathic composition of *Aconitum nap.* 15×, *Arg. nit.* 15×, *Aur. met.* 15×, *Baptisia* 15×, *Bryonia* 15×, *Chelidonium majus* 15×, *Cimicifuga* 15×, Conium 15×, *Gelsemium* 15×, *Ignatia* 15×, Kali carb. 15×, *Lachesis* 15×, *Lilum* 15×, *Lycopodium* 15×, *Nat. carb.* 15×, *Nat. mur.* 15×, *Phosphoricum ac.* 15×, *Phosphorus* 15×, *Picricum ac.* 15×, *Plumb. met.* 15×, *Sepia* 15×, *Staphysag.* 15×, *Stramonium* 15×, *Thuja occ.* 15×, *Zinc. met.* 15×, *Chamomilla* 3×, *Hypericum* 3×, *Valeriana* 3×;

(e) a homeopathic composition of *Anacardium orientale* 15×, *Antimon. crud.* 15×, *Arg. nit.* 15×, *Berber. vulg.* 15×, *Bryonia* 15×, *Chelidonium majus* 15×, *Digitalis* 15×, *Graphites* 15×, Humulus 15×, Iris versicolor 15×, *Kali carb.* 15×, *Lycopodium* 15×, *Nat. carb.* 15×, *Nat. sulphuricum* 15×, *Nux vom.* 15×, *Pulsatilla* 15×, *Rhus toxicodendron* 15×, *Scutellaria laterifolia* 15×, *Sepia* 15×, *Stramonium* 15×, *Chamomilla* 3×, *Passiflora* 3×, *Valeriana* 3×; and (f) a homeopathic composition of *Uricum acidum* 15×, *Benzoicum acidum* 10×, *Berber. vulg.* 10×, *Bryonia* 10×, *Cantharis* 10×, *Carduus benedictus* 10×, *Ceanothus* 10×, *Chelidonium majus* 10×, *Chionanthus virginica* 10×, Cinchona 10×, Dioscorea 10×, Dolichos 10×, Iris versicolor 10×, Juniperus com. 10×, Nux vom. 10×, Ptelea 10×, Taraxacum 10×, Carduus mar. 3×, *Cynara scolymus* 3×, *Solidago* 3×, *Taraxacum* 3×.

20. A method comprising bottling of a homeopathic drinking water formulation made by the method of claim 1, wherein said bottling comprises introducing the homeopathic drinking water formulation into a beverage container, and sealing the beverage container to which the homeopathic drinking water formulation has been introduced, to provide a packaged water formulation.

* * * * *